United States Patent
Neel et al.

(10) Patent No.: US 10,508,309 B2
(45) Date of Patent: Dec. 17, 2019

(54) METHODS FOR DETECTING AND TREATING VARIANTS OF SEBORRHEIC KERATOSES

(71) Applicant: THE GENERAL HOSPITAL CORPORATION, Boston, MA (US)

(72) Inventors: Victor A. Neel, Providence, RI (US); Anna I. Mandinova, Newton, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 14/891,771

(22) PCT Filed: May 16, 2014

(86) PCT No.: PCT/US2014/038330
§ 371 (c)(1),
(2) Date: Nov. 17, 2015

(87) PCT Pub. No.: WO2014/186663
PCT Pub. Date: Nov. 20, 2014

(65) Prior Publication Data
US 2016/0130658 A1 May 12, 2016

Related U.S. Application Data

(60) Provisional application No. 61/824,528, filed on May 17, 2013.

(51) Int. Cl.
*C12Q 1/6886* (2018.01)
*G01N 33/574* (2006.01)

(52) U.S. Cl.
CPC ........ *C12Q 1/6886* (2013.01); *G01N 33/5743* (2013.01); *C12Q 2600/112* (2013.01); *C12Q 2600/158* (2013.01); *G01N 2333/4706* (2013.01)

(58) Field of Classification Search
CPC .............. C12Q 1/6886; C12N 15/1137; G01N 33/5743
See application file for complete search history.

(56) References Cited

U.S. PATENT DOCUMENTS

| | | | | |
|---|---|---|---|---|
| 6,495,582 B1 * | 12/2002 | Hale | ............ | C07D 413/04 514/378 |
| 8,778,935 B2 * | 7/2014 | Pastor Fernandez | ...... | 514/233.2 |
| 8,809,283 B2 | 8/2014 | Arbiser | | |
| 2008/0207545 A1 | 8/2008 | Hoke | | |
| 2009/0004160 A1 | 1/2009 | Park et al. | | |
| 2009/0178153 A1 | 7/2009 | Gaitanaris et al. | | |
| 2011/0230476 A1 * | 9/2011 | Niu | ............ | C12N 9/1205 514/230.5 |
| 2011/0262956 A1 | 10/2011 | Elias et al. | | |
| 2012/0071424 A1 | 3/2012 | Shin et al. | | |
| 2012/0083492 A1 * | 4/2012 | Pastor Fernandez | ............ | C07D 487/04 514/233.2 |
| 2012/0258967 A1 * | 10/2012 | Qiao | ............ | C07D 401/04 514/233.8 |
| 2013/0072500 A1 | 3/2013 | Banka et al. | | |
| 2015/0079107 A1 * | 3/2015 | Mandinova | ............ | A61K 45/06 424/158.1 |

FOREIGN PATENT DOCUMENTS

| | | |
|---|---|---|
| RU | 2148970 C1 | 5/2000 |
| RU | 2342387 C2 | 12/2008 |
| WO | 2005/094322 A2 | 10/2005 |
| WO | 2008/121261 A2 | 10/2008 |
| WO | 2011/128701 A2 | 10/2011 |
| WO | 2013/163512 A1 | 10/2013 |

OTHER PUBLICATIONS

Mandinova et al., (J Clin Invest. Oct. 2009;119(10):3127-37).*
Mandrell et al., (Semin Diagn Pathol. Aug. 2009;26(3):150-63, Abstract Only).*
Heidenreich et al. (2017, Oncogene 8(22):36639-36649).*
Ko et al., "Comparison of benign keratoses using p53, bcl-1 and bcl-2", J Cutan Pathol. 32(5):356-359 (2005). (Abstract Only).
Han et al., "Akt inhibitor A-443654 induces rapid Akt Ser-473 phosphorylation independent of mTORC1 inhibition", Oncogene, 26(38):5655-5661 (2007).
Hafner et al., "High Frequency of FGFR3 Mutations in Adenoid Seborrheic Keratoses", Journal of Investigative Dermatology, 126:2404-2407 (2006).
Hafner et al., "Multiple oncogenic mutations and clonal relationship in spatially distinct benign human epidermal tumors", PNAS, 107(48):20780-20785 (2010).
Hafner et al., "Oncogenic PIK3CA mutations occur in epidermal nevi and seborrheic keratoses with a characteristic mutation pattern", PNAS, 104(33):13450-13454 (2007).
Hernandez et al., "Fibroblast Growth Factor Receptor 3 Mutations in Epidermal Nevi and Associated Low Grade Bladder Tumors", Journal of Investigative Dermatology, 127(7):1664-1666 (2007).
Kolev et al., "EGFR signalling as a negative regulator of Notch1 gene transcription and function in proliferating keratinocytes and cancer", Nature Cell Biology, 10:902-911 (2008).
Kumar et al., "SADDAN syndrome", J Pediatr Endocr Met, 24(9-10):851-852 (2011).
Mandinova et al., "A positive FGFR3/FOXN1 feedback loop underlies benign skin keratosis versus squamous cell carcinoma formation in humans", J. Clin. Invest., 119(10):3127-3137 (2009).
Ming et al., "UVA Induces Lesions Resembling Seborrheic Keratoses in Mice with Keratinocyte-Specific PTEN Down-Regulation", J Invest Dermatol., 131(7):1583-1586 (2011).

(Continued)

*Primary Examiner* — Elizabeth C. Kemmerer
(74) *Attorney, Agent, or Firm* — Nixon Peabody LLP; David S. Resnick; Teresa A. Ptashka (57) ABSTRACT

Disclosed herein are assays and methods for distinguishing a keratoacanthoma from squamous cell carcinoma. Methods for diagnosing a keratoacanthoma are also provided. Methods for treating variants of seborrheic keratoses (i.e., keratoacanthoma, acanthosis nigricans, or epidermal nevus) are also provided.

4 Claims, 4 Drawing Sheets

(56) References Cited

OTHER PUBLICATIONS

Mir et al., "Cutaneous Features of Crouzon Syndrome With Acanthosis Nigricans", JAMA Dermatol., 149(6):737-741 (2013).
Miranda et al., "Analysis of mutations in the PIK3CA and FGFR3 genes in verrucous epidermal nevus", An Bras Dermatol., 88(6 Suppl 1):S36-38 (2013).
Okuzumi et al., "Inhibitor Hijacking of Akt Activation", Nat Chem Biol., 5(7):484-493 (2009).
Rheinwald et al., "Epidermal growth factor and the multiplication of cultured human epidermal keratinocytes", Nature, 265(5593):421-424 (1977).
Rheinwald et al., "Serial Cultivation of Strains of Human Epidermal Keratinocytes: the Formation of Keratinizing Colonies from Single Cells", Cell., 6:331-344 (1975).
Rodrik-Outmezguine et al., "mTOR Kinase Inhibition Causes Feedback-Dependent Biphasic Regulation of AKT Signaling", Cancer Discovery, 1(3):248-259 (2011).
Simionescu et al., "Apoptosis in seborrheic keratoses: an open door to a new dermoscopic score", J. Cell. Mol. Med., 16(6):1223-1231 (2012).
Lindsley et al., "The PI3K/Akt Pathway: Recent Progress in the Development of ATP-Competitive and Allosteric Akt Kinase Inhibitors", Current Cancer Drug Targets 8(1):7-18 (2008).
Chan et al., "Resistance of Akt kinases to dephosphorylation through ATP-dependent conformational plasticity", Proc. Natl. Acad. Sci. USA 108(46):E1120-E1127 (2011).
Grimshaw et al., "AT7867 Is a Potent and Oral Inhibitor of AKT and p70 S6 Kinase That Induces Pharmacodynamic Changes and Inhibits Human Tumor Xenograft Growth", Mol. Cancer Ther. 9(5):1100-1110 (2010).
Nakamura et al., "Enhanced expression of p16 in seborrhoeic keratosis; a lesion of accumulated senescent epidermal cells in G1 arrest", Br. J. Dermatol. 149:560-565 (2003).
Saxty et al. "Identification of inhibitors of protein kinase B using fragment-based lead discovery." Journal of Medicinal Chemistry 50(10):2293-2296 (2007).

* cited by examiner

METHODS FOR DETECTING AND TREATING VARIANTS OF SEBORRHEIC KERATOSES

CROSS-REFERENCE TO RELATED APPLICATION

This application is a 35 U.S.C. § 371 National Phase Entry Application of International Application No. PCT/US14/38330 filed May 16, 2014, which designates the U.S., and claims benefit under 35 U.S.C. § 119(e) of U.S. Provisional Application No. 61/824,528 filed May 17, 2013, the contents of each of which are incorporated herein by reference in their entireties.

TECHNICAL FIELD

The present disclosure relates to treatment methods for variants of seborrheic keratoses such as acanthosis nigricans, keratoacanthomas, and epidermal nevi.

BACKGROUND

Seborrheic keratoses (SKs) are the most common benign epithelial tumors in humans. The etiology of SKs is unknown but they exhibit histologic evidence of increased proliferation of keratinocytes. These lesions have an increased rate of apoptosis and several studies show that their incidence increases with age. Some studies have found that 88% of individuals over age 64 have at least one SK.

SKs are characterized as a dull hyperkeratotic macule that evolves to a papulonodular lesion. They can appear as pale brown, pink, tan or brown in color and the surface can become warty or verrucous. The size varies from 5 mm to several centimeters and a classic "stuck on" appearance is observed. SKs almost never progress to malignant tumors.

SKs commonly harbor multiple oncogenic mutations in FGFR3, PIK3CA, KRAS, HRAS, EGFR, and AKT1 oncogenes but not in tumor suppressor genes p53, TSC1, and PTEN. There is no evidence indicating that a senescence program is activated in SKs. The expression profile of SKs is very similar to malignant skin tumors such as squamous cell carcinomas with the exception that SKs harbor a strong activation of a pro-differentiation program governed by a feedback loop between activated receptor tyrosine kinase signaling (such as FGFR3) and the transcription factor FOXN1.

Acanthosis nigricans (AN) is a brown, velvety plaque that usually arises symmetrically in flexural folds, such as in the axilla, around the neck, in the groin and under the breasts. Sporadic cases are due to several causes, but most commonly to insulin insensitivity and diabetes. Obese individuals are also at risk of developing AN. In addition, several internal malignancies may present clinically with AN.

Keratoacanthomas (KAs) are considered low-grade variants of cutaneous squamous cell carcinoma (SCC). Clinically, they are distinguishable from SCC by these features: (1) a "volcano-like" appearance with a thick keratin plug, (2) being itchy or painful, (3) spontaneous involution with scarring, (4) appearance in surgical scars or in traumatized skin and (5) inability to metastasize. However, histologically they closely resemble well-differentiated SCC and most pathologists are reluctant to diagnose lesions as KA. No special stains are available to aid the pathologist. As a result KAs are treated as if they were malignant and are almost always surgically excised, adding health risks and costs to treatment.

Epidermal nevi (EN) are benign lesions presenting at birth or in childhood. Epidermal nevi are overgrowths of structures and tissue of the epidermis, the outermost layer of the skin. The different types of epidermal nevi can vary in size, number, location, distribution and appearance.

SUMMARY

The invention is based, in part, on the discovery that AN, KAs, and EN are variants of SKs. In one aspect, a method is provided herein for treating a variant of seborrheic keratoses in a subject, the method comprising administering a therapeutically effective amount of a composition that inhibits the Akt signaling pathway.

In some embodiments, the variant of SKs is AN, KA, or EN.

In some embodiments, the composition comprises a small molecule, a peptide inhibitor, or an RNAi molecule.

In some embodiments, the composition is an Akt-1 and/or an Akt-2 inhibitor and/or a pan-Akt inhibitor.

In some embodiments, the therapeutically effective amount of the composition does not substantially affect the survival of normal keratinocytes.

In some embodiments, the composition further comprises a pharmaceutically acceptable carrier.

In some embodiments, the composition is applied topically or administered systemically.

In another aspect, a method is provided herein for inducing apoptosis in an AN cell, a KA cell, or an EN cell, the method comprising contacting the AN cell, the KA cell, or the EN cell with an effective amount of a composition that inhibits Akt signaling.

In some embodiments, the composition comprises a small molecule, a peptide inhibitor, or an RNAi molecule.

In some embodiments, the composition is an Akt-1 and/or an Akt-2 inhibitor and/or a pan-Akt inhibitor.

In yet another aspect, an assay is provided herein for distinguishing a KA from SCC, the assay comprising: (i) measuring, in a sample obtained from a subject, a level of FOXN1; (ii) comparing the level of FOXN1 with a reference level; and (iii) identifying the subject as having a KA if the level of FOXN1 is significantly higher than the reference level.

In some embodiments, the assay further comprises providing a treatment based on the level of FOXN1 and appropriate for a KA.

In some embodiments, the treatment comprises administering a therapeutically effective amount of a composition that inhibits the Akt signaling pathway.

In some embodiments, the sample is a skin biopsy.

In some embodiments, the level of FOXN1 is measured by an immunoassay.

In some embodiments, the level of FOXN1 is measured by measuring a level of FOXN1 mRNA.

In some embodiments, the level of FOXN1 mRNA is measured by reverse transcription-polymerase chain reaction (RT-PCR).

A related aspect of the invention relates to a method of diagnosing a KA in a subject, the method comprising (i) assaying a level of FOXN1 in a sample obtained from the subject; (ii) comparing the level of FOXN1 with a reference level; and (iii) identifying the subject as having a KA if the level of FOXN1 is significantly higher than the reference level.

In some embodiments, the method further comprises determining that the subject does not have a SK.

In some embodiments, the sample is a skin biopsy.

In some embodiments, the level of FOXN1 is measured by an immunoassay.

In some embodiments, the level of FOXN1 is measured by measuring a level of FOXN1 mRNA.

In some embodiments, the level of FOXN1 mRNA is measured by reverse transcription-polymerase chain reaction (RT-PCR).

In some embodiments, the method further comprises providing a treatment based on the level of FOXN1 and appropriate for a KA.

In some embodiments, the treatment comprises administering a therapeutically effective amount of a composition that inhibits the Akt signaling pathway.

In another aspect, a method is provided herein that comprises selecting a subject with AN, a KA, or an EN, and administering to the subject a therapeutically effective amount of a composition that inhibits the Akt signaling pathway.

In some aspects of all embodiments, the subject is a mammal.

In some aspects of all embodiments, the mammal is a human.

BRIEF DESCRIPTION OF THE DRAWINGS

FIGS. 2A-2C are plots comparing the relative mRNA levels of FOXN1 in SK cells (FIG. 2A), SCC cells (FIG. 2B), and KA cells (FIG. 2C) to normal skin cells. In FIG. 2C, HKC stands for normal human keratinocyte.

DETAILED DESCRIPTION

The assays and methods provided herein are based, in part, on the discovery that acanthosis nigricans (AN), keratoacanthomas (KAs), and epidermal nevi (EN) are variants of seborrheic keratoses (SKs). Without wishing to be bound by theory, AN, KAs, and EN exhibit, in some aspects, similar molecular characteristics to SKs, and thus providing credible support for the conclusion that AN, KAs, and EN are variants of SKs.

Figure 3A:
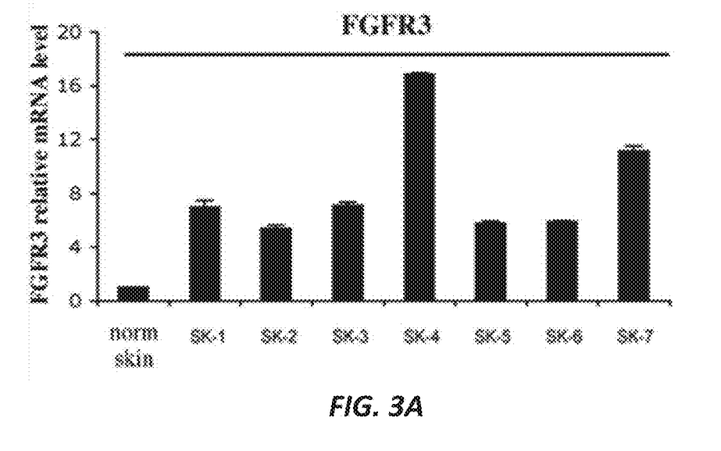
FIGS. 3A-3B are plots comparing the relative mRNA levels of FGFR3 in SK cells (FIG. 3A) and SCC cells (FIG. 3B) to normal skin cells.
Figure 3B:
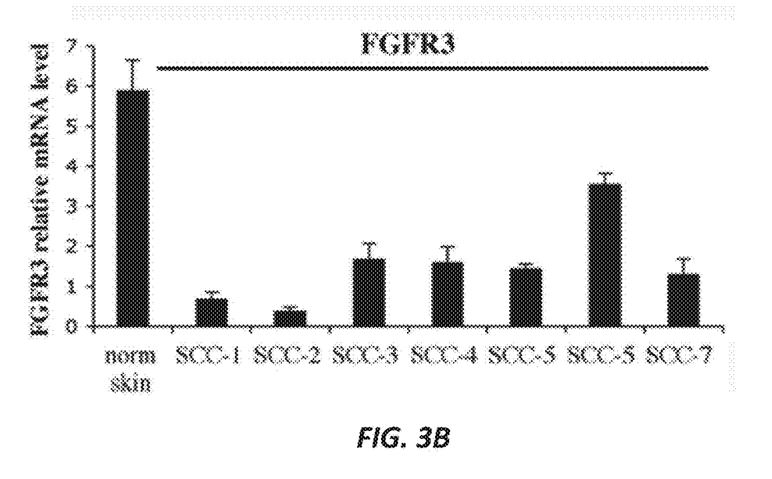

In the case of AN, histologically, AN resembles SKs. Further, several genetic syndromes such as familial AN, Crouzon's syndrome, SADDAN syndrome, and thanotophoric dysplasia, include AN as a constant clinical feature. Notably, these genetic syndromes are due to activating mutations in FGFR3 (for example, see Mir et al., JAMA Dermatol. 2013, April 9:1-5; Kumar et al., J. Pediatr. Endocrinol. Metab. 2011, 24(9-10): 851-852). Most SKs have also been found to have activating mutations in the receptor kinase FGFR3 (FIG. 3A).

In the case of EN, histologically, EN also resembles SKs. In addition, EN exhibits the same mutations in the PIK3CA and FGFR3 genes as SKs (Miranda et al., An Bras Dermatol. 2013, 88, 36-38; Hafner et al., Proc. Natl. Acad. Sci. USA 2007, 104, 13450-13454; Hernandez et al., J. Invest. Dermatol. 2007, 127, 1664-1666).

Figure 1:
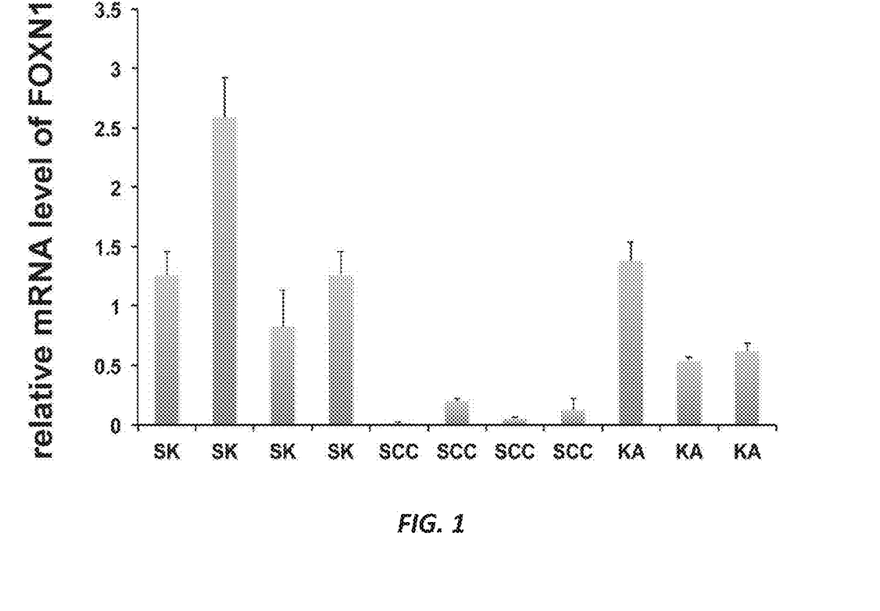
FIG. 1 is a plot showing the relative mRNA levels of forkhead box N1 (FOXN1) in seborrheic keratosis (SK) cells, squamous cell carcinoma (SCC) cells, and keratoacanthoma (KA) cells. The mRNA level of FOXN1 is significantly higher in SK cells and KA cells than in SCC cells.
Figure 2A:
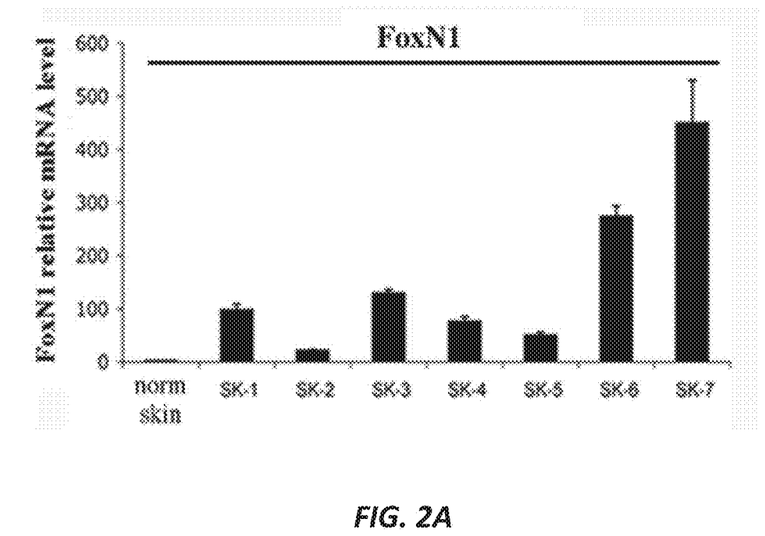
Figure 2B:
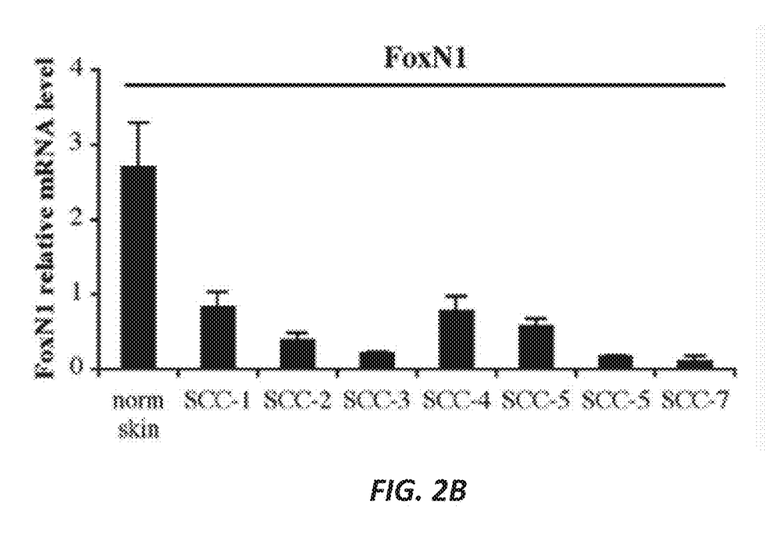
Figure 2C:
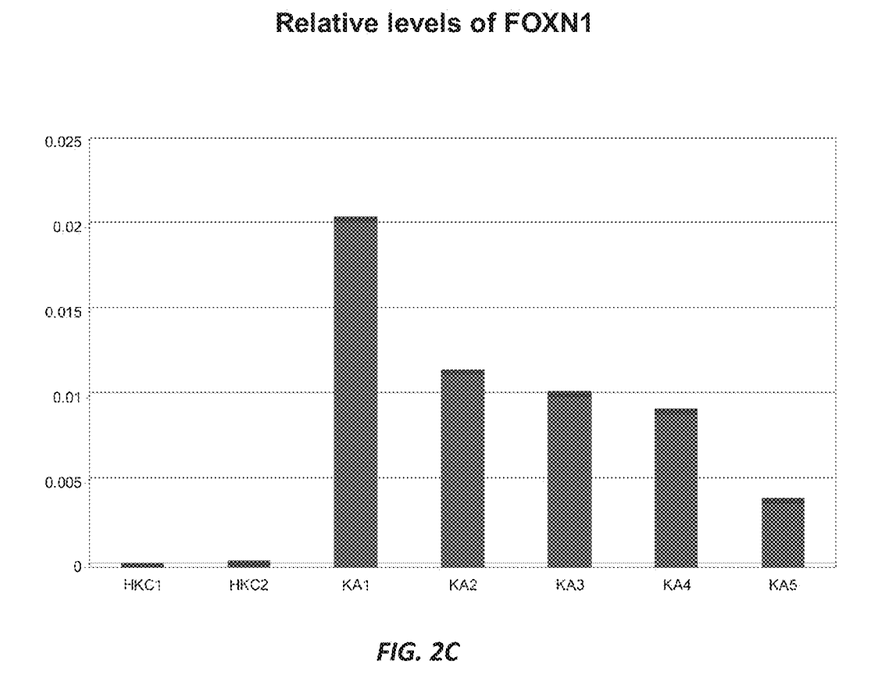

In the case of KAs, both KAs and SKs have been found to have significantly higher levels of FOXN1 compared to SCC (FIGS. 1 and 2). Table 1 in the Example compares the features of KA, SK, and SCC.

As many KAs are misdiagnosed as squamous cell carcinoma, an assay is thus provided herein for distinguishing a KA from SCC, the assay comprising: (i) measuring, in a sample obtained from a subject, a level of FOXN1; (ii) comparing the level of FOXN1 with a reference level; and (iii) identifying the subject as having a KA if the level of FOXN1 is significantly higher than the reference level.

In some embodiments, the sample is a skin biopsy. There are several types of skin biopsies that include, but are not limited to, a shave biopsy, a punch biopsy, an incisional biopsy, an excisional biopsy, a curettage biopsy, a needle aspiration biopsy, and a saucerization biopsy.

Exemplary FOXN1 amino acid and nucleotide sequences (including human and other mammalian species) are available, e.g., from Schorpp et al. (1997) Immunogenetics 46 (6), 509-515 and GENBANK® entry O15353 [GI: 13124629]. The protein has a winged-helix DNA binding domain located at about amino acids 271 to 367 or about 271 to 349. Exemplary fragments of the human FOXN1 protein include fragments that include, or consist of, about amino acids 1-270, 10-180, 271-367, 271-349, 350-648, 368-648, 400-550, and 500-640. Such fragments can be fused to heterologous amino acids, e.g., sequences other than FOXN1.

Methods for measuring the level of FOXN1 are known in the art and include, but are not limited to, antibody based assays such as enzyme immunoassays (EIA), radioimmunoassays (RIA), and Western blot analysis. The level of FOXN1 can also be quantified by measuring the FOXN1 mRNA levels. Methods for measuring the FOXN1 mRNA levels include, but are not limited to polymerase chain reaction (PCR, e.g., quantitative or semi-quantitative, or reverse transcription-PCR), hybridization assay, Northern blotting, primer extension, and ribonuclease protection.

The term "reference level" is used herein to refer to the level of expression of a protein (e.g., FOXN1) in a known sample against which another sample is compared (e.g., a skin sample obtained from a subject suspected of having a KA). In some embodiments, the reference level can be a level of FOXN1 in a sample (e.g., a skin biopsy) of a healthy subject with no signs or symptoms of a skin disorder. For example, the healthy subject does not have a SK, KA, EN, or SCC. This would be a "normal" level. In some embodiments, the reference level can be a level of FOXN1 in a sample of a subject having SCC. In some embodiments, the reference level can be a level of FOXN1 in a control sample, a pooled sample of control individuals, or a numeric value or range of values based on the same.

In some embodiments, the level of FOXN1 measured in a sample from a subject identified as having a KA can be at least 10% higher than the reference level, at least 20% higher than the reference level, at least 30% higher than the reference level, at least 40% higher than the reference level, at least 50% higher than the reference level, at least 60% higher than the reference level, at least 70% higher than the reference level, at least 80% higher than the reference level, at least 90% higher than the reference level, at least 100% higher than the reference level, at least 200% higher than the reference level, or at least 500% higher than the reference level.

It should be noted that the reference level can be different, depending on factors such as gender, age, weight, and ethnicity. Thus, reference levels accounting for these and other variables can provide added accuracy for the methods described herein.

In some embodiments, the assay further comprises providing a treatment based on the level of FOXN1 and appropriate for a KA.

A related aspect of the invention relates to a method of diagnosing a KA in a subject, the method comprising (i) assaying a level of FOXN1 in a sample obtained from the subject; (ii) comparing the level of FOXN1 with a reference level; and (iii) identifying the subject as having a KA if the level of FOXN1 is significantly higher than the reference level. In some embodiments, the method provided herein can be used in conjunction with other methods for KA diagnosis such as pathology. In some embodiments, the subject does not have a SK. In some embodiments, the sample is a skin biopsy taken from the part of skin suspected of having KA.

In another aspect, a method is provided herein for treating a variant of SKs in a subject, the method comprising administering a therapeutically effective amount of a composition that treats SKs. Exemplary compositions for treating SKs are disclosed in US20130338226, U.S. Pat. Nos. 6,673,843, and 6,171,593, the contents of each of which are incorporated herein by reference in its entirety.

In some preferred embodiments, the composition inhibits the Akt signaling pathway. Methods of treating a SK using a composition that inhibits the Akt signaling pathway have been disclosed in WO2013163512, the contents of which are incorporated herein by reference in its entirety.

In some embodiments, the variant of SKs is AN, KA, or EN. In some embodiments, the method further comprises selecting a subject having AN, KA, or EN. AN can usually be diagnosed by visual examination of the skin. In rare cases, a skin biopsy can be used for diagnosis. Other tests for AN can include, but are not limited to, blood tests (e.g., measuring blood sugar level), endoscopy, and X-rays. KA can be diagnosed by a physical examination, a pathology test, the assay described herein, or a combination thereof. EN can be diagnosed by skin biopsies, blood tests, urinalysis, x-rays, ultrasound, computed tomography (CT) scans or magnetic resonance imaging (MRI), electroencephalograms (EEG), and a combination thereof.

Inhibition of Akt

Akt, also known as protein kinase B (PKB), is a serine-threonine protein kinase that is regulated by phosphatidylinositol 3,4,5-triphosphate (PIP3) and has been implicated in signaling of survival in a wide variety of cells, including fibroblastic, epithelial, and neuronal cells (Franke et al. Cell 1997; 1; 88:435-7; Hemmings et al. Science 1997; 275:628-30). Akt was first recognized as an anti-apoptotic factor during analysis of signaling by insulin-like growth factor-1 (IGF-1), which promotes the survival of cerebellar neurons (Dudek et al. Science 1997; 275:661-5). IGF-1 was shown to activate PI3-kinase-triggered activation of the serine-threonine kinase, Akt. Activated Akt signaling is critical in promoting cell survival downstream of growth factors, oncogenes and cell stress. Akt enhances the survival of cells by blocking the function of pro-apoptotic pathways such as the p53-MDM2 pathways as well as the FOXO mediated pro-apoptotic cascade. The family members of Akt include, but are not limited to, Akt1, Akt2, and Akt3.

Further definition and details of the PI3 kinase/Akt signaling pathway are disclosed in the art e.g., Downward, J. Curr. Opin. Cell Biol. 10, 262-267(1988); Jimenez, C. et al., J. Biol. Chem. 277(44):41556-41562 (2002); Kitamura, T. et al., Mol. Cell Biol. 19, 6286-6296 (1999); Ruggero D. and Sonenberg N. Oncogene. 24, 7426-34 (2005); Testa J. R. and Tsichlis P. N. Oncogene. 7391-7393 (2005); and Zhou X. M. et al., J. Biol. Chem. 275, 25046-25051 (2000).

By "inhibits Akt-1 and/or Akt-2 expression" is meant that the amount of expression of Akt-1 and/or Akt-2 is at least 5% lower in populations treated with an Akt signaling pathway inhibitor, than a comparable, control population, wherein no such inhibitor is present. It is preferred that the percentage of Akt expression (e.g., Akt-1 and/or Akt-2) in an inhibitor-treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no inhibitor is added.

By "inhibits Akt activity" is meant that the amount of functional activity of Akt-1 and/or Akt-2 is at least 5% lower in populations treated with an Akt or Akt signaling pathway inhibitor, than a comparable, control population, wherein no such inhibitor is present. It is preferred that the percentage of Akt activity (e.g., Akt-1 and/or Akt-2 activity) in an inhibitor-treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no Akt or Akt signaling pathway inhibitor is added. At a minimum, Akt activity can be assayed by determining the amount of Akt expression at the protein or mRNA levels, using techniques standard in the art. Alternatively, or in addition, Akt activity can be determined using a reporter construct, wherein the reporter construct is sensitive to Akt activity.

In one embodiment, the inhibitor of Akt activity is selected from the group consisting of an antibody against Akt-1 and/or Akt-2 (including an antibody that acts as a pan-Akt inhibitor) or an antigen-binding fragment thereof, a small molecule, and a nucleic acid. In one embodiment, the nucleic acid is an Akt-1 and/or Akt-2 specific RNA interference agent, a vector encoding the RNA interference agent, or an aptamer that binds Akt-1 and/or Akt-2.

In one embodiment, the inhibitor of Akt activity interferes with Akt interactions with its downstream mediators. In one embodiment, the downstream mediators are GSK3, FoxO3, MDM2, among others.

Antibody Inhibitors of the Akt Signaling Pathway

Antibodies that specifically bind Akt or an Akt downstream mediator can be used to inhibit the Akt signaling pathway in vivo, in vitro, or ex vivo. Antibodies to Akt are commercially available and/or can be raised by one of skill in the art using well known methods. The Akt inhibitory activity of a given antibody, or, for that matter, any Akt inhibitor, can be assessed using methods known in the art or described herein—to avoid doubt, an antibody that inhibits Akt will cause an increase in cell death. Antibody inhibitors of Akt can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art.

An "antibody" that can be used according to the methods described herein includes complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies. Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred. Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific. Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen.

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., 1988. While both polyclonal and monoclonal antibodies can be used in the methods described herein, it is preferred that a monoclonal antibody is used where conditions require increased specificity for a particular protein.

Nucleic Acid Inhibitors of Akt Expression

A powerful approach for inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g. the Akt1 or Akt2 sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, according to Jackson et al. (Id.), 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human Akt1 or Akt2 mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

In a preferred embodiment, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells after transcription into siRNA capable of targeting, for example, Akt-1 or Akt-2.

In one embodiment, the vector is a regulatable vector, such as tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In one embodiment, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is catheterization of the blood supply vessel of the target organ. Other strategies for delivery of the RNA interference agents, e.g., the siRNAs or shRNAs used in the methods of the invention, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles. The RNA interference agents, e.g., the siRNAs targeting Akt-1 or Akt-2 mRNA, may be delivered singly, or in combination with other RNA interference agents, e.g., siRNAs, such as, for example siRNAs directed to other cellular genes. Akt siRNAs may also be administered in combination with other pharmaceutical agents which are used to treat or prevent diseases or disorders associated with oxidative stress, especially respiratory diseases, and more especially asthma. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA. The targeted region of the siRNA molecule of the present invention can be selected from a given target gene sequence, e.g., an Akt-1 or Akt-2 coding sequence, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al., (2001) supra and Elbashir et al., 2001 supra). Analysis of sequence databases, including but not limited to the NCBI, BLAST, Derwent and GenSeq as well as commercially available oligosynthesis companies such as Oligoengine®, may also be used to select siRNA sequences against EST libraries to ensure that only one gene is targeted.

siRNA sequences to target Akt-1, Akt-2, Akt-3, FOXO3, and p53, among others, can also be obtained commercially from e.g., INVITROGEN™, THERMO SCIENTIFIC™, ORIGENE™, among others. For example, Validated Stealth siRNAs can be obtained for Akt-1 (cat. No. VHS40082), Akt-2 (cat. No. VHS41339), and Akt-3 (cat no. HSS115178) from INVITROGEN™. In addition, ON-TARGETplus SMARTpool siRNAS™ can be obtained from THERMO SCIENTIFIC™ for FOXO3 (Human FOXO3A(2309); cat no. L-003007-00-0005) and for p53 (Human TP53 (7157); cat. no. L-003329-00-0005).

Delivery of RNA Interfering Agents

Methods of delivering RNA interference agents, e.g., an siRNA, or vectors containing an RNA interference agent, to the target cells, e.g., AN, KA, or EN cells, skin cells, or other desired target cells, for uptake include injection of a composition containing the RNA interference agent, e.g., an siRNA, or directly contacting the cell, e.g., an AN, KA, or EN cell, with a composition comprising an RNA interference agent, e.g., an siRNA. In another embodiment, RNA interference agent, e.g., an siRNA may be injected directly into any blood vessel, such as vein, artery, venule or arteriole, via, e.g., hydrodynamic injection or catheterization. Administration may be by a single injection or by two or more injections. The RNA interference agent is delivered in a pharmaceutically acceptable carrier. One or more RNA interference agent may be used simultaneously. In one embodiment, a single siRNA that targets human Akt is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., lymphocytes or other cells, inhibit annealing of single strands, stabilize single strands, or otherwise facilitate delivery to the target cell and increase inhibition of the target gene, e.g., Akt-1 or Akt-2. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

In one embodiment, the AN cell, KA cell, or EN cell is contacted ex vivo or in vivo. In one embodiment, the composition inhibits Akt-1 and/or Akt-2 expression.

Small Molecule Inhibition of the Akt Signaling Pathway

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds)

having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Essentially any small molecule inhibitor of the Akt signaling pathway can be used in the treatment of AN, KAs, or EN using the methods described herein. In one embodiment, the small molecule inhibitor of the Akt signaling pathway is an inhibitor of Akt-1, Akt-2, Akt-3 or a combination thereof. In another embodiment, the small molecule inhibitor of the Akt signaling pathway is an ATP-competitive Akt inhibitor. In another embodiment, the ATP-competitive Akt inhibitor reduces phosphorylation of GSK-3β.

Some non-limiting examples of small molecule compounds useful in the treatment of AN, KAs, or EN as described herein include kaempferol, ellipticine (with Akt inhibition), nutlin-3 and puromycin.

Apoptosis

Apoptosis is a mechanism for programmed cell death that typically occurs during embryogenesis, development and during the normal physiological response to aging. Apoptosis can also be triggered in response to a cell stressor, such as heat, radiation, nutrient deprivation, viral infection, hypoxia, increased intracellular calcium concentration and in response to certain glucocorticoid receptor activation. Apoptosis, in part, initiates activation of one or more caspase signaling pathways. Caspases are strong proteases that cleave after aspartic acid residues and once activated, are responsible for proteolytic cleavage of a broad spectrum of cellular targets that ultimately lead to cell death. Defective apoptosis regulation can lead to a variety of disorders. For example, impaired apoptotic activity can lead to inappropriate cell survival, and is associated with tumor growth, cancer, autoimmune disease, and inflammatory disease. Conversely, pathologically high levels of apoptosis can result in abnormal initiation of cell death pathways, as observed in e.g., neurodegenerative diseases (e.g., Parkinson's disease, Alzheimer's disease, dementia, and cerebral ischemia, among others) and infection (e.g., AIDS).

Proteins involved in the regulation of apoptosis include, for example, caspase-3, caspase-6, caspase-9, and PARP, among others. Such proteins can be used in immunoassays to detect apoptosis in a cell or tissue.

Other exemplary assays for determining the presence and/or the level of apoptosis in a sample include, but are not limited to, apoptosis is measured using sulforhodamine B (SRB) assay, MTT tetrazolium dye, TUNEL staining, Annexin V staining, propidium iodide staining, DNA laddering, PARP cleavage, caspase activation, and/or assessment of cellular and nuclear morphology.

One aspect of the invention relates to a method for inducing apoptosis in an AN cell, a KA cell, or an EN cell, the method comprising contacting the AN cell, KA cell, or EN cell with an effective amount of a composition that inhibits Akt signaling.

In some embodiments, the contacting is ex vivo. In some embodiments, the contacting is in vivo.

Dosage, Administration and Efficacy

As used herein, "administered" refers to the placement of a composition that induces apoptosis (e.g., an inhibitor of the Akt signaling pathway) into a subject by a method or route which results in at least partial localization of the inhibitor at a desired site. A composition which induces apoptosis can be administered by any appropriate route which results in effective treatment in the subject, i.e. administration results in delivery to a desired location in the subject where at least a portion of the composition delivered, i.e. at least one agent which inhibits Akt, is active in the desired site for a period of time. The period of time the inhibitor is active depends on the half life in vivo after administration to a subject, and can be as short as a few hours, e. g. twenty-four hours, to a few days, to as long as several years. Modes of administration include injection, infusion, instillation, topical or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In one embodiment, the mode of administration is topical.

In a method for treating AN, KA, or EN, an effective amount of composition that induces apoptosis is administered to a patient diagnosed as having one or more AN, KAs, or EN. In one embodiment, the subject can be a mammal (e.g., a primate or a non-primate mammal). In another embodiment, the mammal can be a human, although the approach can be effective with respect to all mammals. In one embodiment, the method comprises administering to the primate subject (e.g., a human) an effective amount of a pharmaceutical composition comprising an agent that induces apoptosis. An "effective amount" means an amount or dose generally sufficient to bring about the desired therapeutic or prophylactic benefit in subjects undergoing treatment. Effective amounts or doses of an agent that induces apoptosis for treatment as described herein can be ascertained by routine methods such as modeling, dose escalation studies or clinical trials, and by taking into consideration routine factors, e.g., the mode or route of administration of agent delivery, the pharmacokinetics of the composition, the severity and course of the disorder or condition, the subject's previous or ongoing therapy, the subject's health status and response to drugs, and the judgment of the treating physician. An exemplary dose for a human is in the range of from about 0.001 to about 1 g of subject's body weight per day.

While the dosage range for the composition comprising an agent that induces apoptosis depends upon the potency of the composition, and includes amounts large enough to produce the desired effect (e.g., increase in cell death), the dosage should not be so large as to cause unacceptable adverse side effects. Generally, the dosage will vary with the formulation (e.g., oral, topical, i.v. or subcutaneous formulations), and with the age, condition, and sex of the patient. The dosage can be determined by one of skill in the art and can also be adjusted by the individual physician in the event of any complication. Typically, the dosage will range from 0.001 mg/day to 500 mg/day. In some embodiments, the dosage range is from 0.001 mg/day to 400 mg/day, from 0.001 mg/day to 300 mg/day, from 0.001 mg/day to 200 mg/day, from 0.001 mg/day to 100 mg/day, from 0.001 mg/day to 50 mg/day, from 0.001 mg/day to 25 mg/day, from 0.001 mg/day to 10 mg/day, from 0.001 mg/day to 5 mg/day, from 0.001 mg/day to 1 mg/day, from 0.001 mg/day to 0.1 mg/day, from 0.001 mg/day to 0.005 mg/day. Alternatively, the dose range will be titrated to maintain serum levels between 5 µg/mL and 30 µg/mL. Administration of the doses recited above can be repeated for a limited period of time or as necessary. In some embodiments, the doses are given or applied once a day, or multiple times a day, for example but not limited to three times a day. In one embodiment, the doses recited above are administered daily for several weeks or months. The duration of treatment depends upon the subject's clinical progress and responsiveness to therapy. Continuous, relatively low maintenance doses are contemplated after an initial higher therapeutic dose. Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. The composition can also be administered systemically. Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The efficacy of a treatment comprising an agent that induces apoptosis in the treatment of AN, KAs, or EN can be determined by the skilled clinician. However, a treatment is considered "effective treatment," as the term is used herein, if any one or all of the signs or symptoms of, as but one example, appearance of AN, KAs, or EN are altered in a beneficial manner, other clinically accepted symptoms or markers of disease are improved or ameliorated, e.g., by at least 10% following treatment with an inhibitor. Methods of measuring these indicators are known to those of skill in the art and/or described herein.

Some embodiments of the invention are listed in the following paragraphs:

I. A method of treating a variant of seborrheic keratoses in a subject, the method comprising administering a therapeutically effective amount of a composition that inhibits an Akt signaling pathway.

II. The method of paragraph I, wherein the variant of seborrheic keratoses is acanthosis nigricans, keratoacanthoma, or epidermal nevus.

III. The method of paragraph I or II, wherein the composition comprises a small molecule, a peptide inhibitor, or an RNAi molecule.

IV. The method of any of paragraphs I to III, wherein the composition is an Akt-1 and/or an Akt-2 inhibitor and/or a pan-Akt inhibitor.

V. The method of any of paragraphs I to IV, wherein the therapeutically effective amount of the composition does not substantially affect the survival of normal keratinocytes.

VI. The method of any of paragraphs I to V, wherein the composition further comprises a pharmaceutically acceptable carrier.

VII. The method of any of paragraphs I to VI, wherein the composition is applied topically or administered systemically.

VIII. The method of any of paragraphs I to VII, wherein the subject is a mammal.

IX. The method of paragraph VIII, wherein the mammal is a human.

X. A method for inducing apoptosis in an acanthosis nigricans cell, a keratoacanthoma cell, or an epidermal nevus cell, the method comprising contacting the acanthosis nigricans cell, keratoacanthoma cell, or epidermal nevus cell with an effective amount of a composition that inhibits Akt signaling.

XI. The method of paragraph X, wherein the composition comprises a small molecule, a peptide inhibitor, or an RNAi molecule.

XII. The method of paragraph X or XI, wherein the composition is an Akt-1 and/or an Akt-2 inhibitor and/or a pan-Akt inhibitor.

XIII. An assay for distinguishing a keratoacanthoma from squamous cell carcinoma (SCC), the assay comprising
(i) measuring, in a sample obtained from a subject, a level of forkhead box protein N1 (FOXN1);
(ii) comparing the level of FOXN1 with a reference level; and
(iii) identifying the subject as having a keratoacanthoma if the level of FOXN1 is significantly higher than the reference level.

XIV. The assay of paragraph XIII, further comprising providing a treatment based on the level of FOXN1 and appropriate for a keratoacanthoma.

XV. The assay of paragraph XIV, wherein the treatment comprises administering a therapeutically effective amount of a composition that inhibits an Akt signaling pathway.

XVI. The assay of any of paragraphs XIII to XV, wherein the sample is a skin biopsy.

XVII. The assay of any of paragraphs XIII to XVI, wherein the level of FOXN1 is measured by an immunoassay.

XVIII. The assay of any of paragraphs XIII to XVI, wherein the level of FOXN1 is measured by measuring a level of FOXN1 mRNA.

XIX. The assay of paragraph XVIII, wherein the level of FOXN1 mRNA is measured by reverse transcription-polymerase chain reaction (RT-PCR).

XX. The assay of any of paragraphs XIII to XIX, wherein the subject is a mammal.

XXI. The assay of paragraph XX, wherein the mammal is a human.

XXII. A method of diagnosing a keratoacanthoma in a subject, the method comprising
(i) assaying a level of FOXN1 in a sample obtained from the subject;
(ii) comparing the level of FOXN1 with a reference level; and
(iii) identifying the subject as having a keratoacanthoma if the level of FOXN1 is significantly higher than the reference level.

XXIII. The method of paragraph XXII, further comprising determining that the subject does not have a seborrheic keratosis.

XXIV. The method of paragraph XXII or XXIII, wherein the sample is a skin biopsy.

XXV. The method of any of paragraphs XXII to XXIV, wherein the level of FOXN1 is measured by an immunoassay.

XXVI. The method of any of paragraphs XXII to XXIV, wherein the level of FOXN1 is measured by measuring a level of FOXN1 mRNA.

XXVII. The method of paragraph XXVI, wherein the level of FOXN1 mRNA is measured by reverse transcription-polymerase chain reaction (RT-PCR).

XXVIII. The method of any of paragraphs XXII to XXVII, further comprising providing a treatment based on the level of FOXN1 and appropriate for a keratoacanthoma.

XXIX. The method of paragraph XXVIII, wherein the treatment comprises administering a therapeutically effective amount of a composition that inhibits an Akt signaling pathway.

XXX. The method of any of paragraphs XX to XIX, wherein the subject is a mammal.

XXXI. The method of paragraph XXX, wherein the mammal is a human.

XXXII. A method comprising
(i) selecting a subject with acanthosis nigricans, a keratoacanthoma, or an epidermal nevus; and
(ii) administering to the subject a therapeutically effective amount of a composition that inhibits an Akt signaling pathway.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

The term "disease", "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, affectation.

The term "sample" or "biological sample" as used herein denotes a sample taken or isolated from a biological organism, e.g., a skin biopsy from a subject. Exemplary biological samples include, but are not limited to, a biofluid sample; blood; serum; plasma; urine; saliva; a tumor sample; a biopsy; a tumor biopsy and/or tissue sample etc. The term also includes a mixture of the above-mentioned samples. The term "sample" also includes untreated or pretreated (or pre-processed) biological samples. In some embodiments, a sample can comprise one or more cells from the subject.

The term "statistically significant" or "significantly" refers to statistical significance and generally means a two standard deviation (2 SD) above normal, or higher concentration of the marker present. The term refers to statistical evidence that there is a difference. It is defined as the probability of making a decision to reject the null hypothesis when the null hypothesis is actually true. The decision is often made using the p-value. The level of statistical significant can be, for example, of at least $p<0.05$, of at least $p<0.01$, of at least $p<0.005$, or of at least $p<0.001$.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body without the production of undesirable physiological effects such as nausea, dizziness, gastric upset and the like. Each carrier must also be "acceptable" in the sense of being compatible with the other ingredients of the formulation. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. The pharmaceutical formulation contains a compound as described herein in combination with one or more pharmaceutically acceptable ingredients. The carrier can be in the form of a solid, semi-solid or liquid diluent, cream or a capsule. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. The terms such as "excipient", "carrier", "pharmaceutically acceptable carrier" or the like are used interchangeably herein.

By "treatment", "prevention" or "amelioration" of a condition, disease, or disorder is meant delaying or preventing the onset of such a disease or disorder, reversing, alleviating, ameliorating, inhibiting, slowing down or stopping the progression, aggravation or deterioration the progression or severity of a condition associated with such a skin disease or disorder (e.g., AN, KAs, or EN). In one embodiment, at least one symptom of a disease or disorder is alleviated by at least 5%, at least 10%, at least 20%, at least 30%, at least 40%, or at least 50%.

The term "treatment", with respect to treatment of a skin disease or disorder (e.g., AN, KAs, or EN) refers to, inter alia, preventing the development of the skin disease or disorder (e.g., AN, KAs, or EN), or altering the course of the skin disease or disorder (e.g., AN, KAs, or EN) (for example, but not limited to, slowing the progression of AN, KAs, or EN), or reversing a symptom of the skin disease or disorder (e.g., AN, KAs, or EN), or reducing one or more symptoms and/or one or more biochemical markers (e.g., FOXN1 for keratoacanthomas) in a subject, preventing one or more symptoms from worsening or progressing, promoting recovery or improving prognosis, and/or preventing the skin disease or disorder (e.g., AN, KAs, or EN) in a subject who is free therefrom as well as slowing or reducing progression of existing skin disease or disorder (e.g., AN, KAs, or EN). For a given subject, improvement in a symptom, its worsening, regression, or progression can be determined by an objective or subjective measure.

Further, as used herein, the terms "treat" or "treatment" refer to both therapeutic treatment and prophylactic or preventative measures, wherein the object is to prevent or slow down (lessen) an undesired physiological change or disorder, such as the progression of the skin disease or disorder (e.g., AN, KAs, or EN), diminishment of extent of disease, stabilized (i.e., not worsening) state of disease, delay or slowing of disease progression, amelioration or palliation of the disease state, and remission (whether partial or total), whether detectable or undetectable. Any particular treatment regimen can provide one or more such clinical results in one or more patients, and need not provide all such clinical results. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically-effective amount" or "effective amount" as used herein means that amount of a composition which is effective for producing some desired therapeutic effect in at least a sub-population of cells in an animal at a reasonable benefit/risk ratio applicable to any medical treatment. For example, an amount of a composition administered to a subject that is sufficient to produce a statistically significant, measurable change in at least one symptom of AN, KAs, or EN.

In connection with contacting a cell with an inhibitor of the Akt signaling pathway, "inducing apoptosis" or "increasing cell death" in a cell indicates that cell death via the apoptotic pathway in a population of cells is at least 5% higher in populations treated with an inhibitor of the Akt signaling pathway, than in a comparable, control population, wherein no Akt signaling pathway inhibitor is present. It is preferred that the percentage of cell death in an Akt signaling pathway inhibitor treated population is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the Akt signaling pathway inhibitor.

By "apoptosis" is meant a cell death pathway wherein a dying cell displays a set of well-characterized biochemical hallmarks that include cytolemmal membrane blebbing, cell soma shrinkage, chromatin condensation, nuclear disintegration, and DNA laddering. There are many well-known assays for determining the apoptotic state of a cell, including, and not limited to: reduction of MTT tetrazolium dye, TUNEL staining, Annexin V staining, propidium iodide staining, DNA laddering, PARP cleavage, caspase activation, and assessment of cellular and nuclear morphology. Any of these or other known assays may be used in the methods of the invention to determine whether a cell is undergoing apoptosis.

An "inhibitor" of the Akt signaling pathway, as the term is used herein, can function in a competitive or non-competitive manner, and can function, in one embodiment, by interfering with the expression of the Akt protein (e.g., Akt-1 and/or Akt-2) and/or a downstream protein in the Akt pathway (e.g., FoxO3, GSK3, MDM2, etc.). Any of a number of different approaches can be taken to inhibit Akt protein expression or activity. An Akt pathway inhibitor includes any chemical or biological entity that, upon treatment of a cell, results in inhibition of the biological activity caused by activation of Akt in response to cellular signals. Akt pathway inhibitors, include, but are not limited to, small molecules, antibodies or antigen-binding antibody fragments, intrabodies, aptamers, antisense constructs, RNA interference agents, and ribozymes.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentiviruses, adenoviruses and adeno-associated viruses), which serve equivalent functions. In one embodiment, lentiviruses are used to deliver one or more siRNA molecule of the present invention to a cell.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the RNA interfering agents may be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding the siRNA molecule directed against the mutant allele, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates may be used to synthesize, in vivo, both sense and antisense strands of siRNAs which effect RNAi (Sui, et al. (2002) PNAS 99(8):5515).

As used herein, a "subject" means a human or animal. Usually the animal is a vertebrate such as, but not limited to a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Subject includes any subset of the foregoing, e.g., all of the above, but excluding one or more groups or species such as humans, primates or rodents. In certain embodiments of the aspects described herein, the subject is a mammal, e.g., a primate, e.g., a human. A subject can be male or female. Additionally, a subject can be an infant or a child.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are described herein.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology described herein is further illustrated by the following examples which in no way should be construed as being further limiting.

Example: Summary of Features for KA, SK, and SCC

The following table lists some of the important features for KA, SK, and SCC. By comparing these features, KA appears to be more similar to SK.

TABLE 1

Summary of features for KA, SK, and SCC.

| Feature | KA | SK | SCC |
|---|---|---|---|
| Clinically benign? | Yes | Yes | No |
| Histologic atypia? | Yes | No | Yes |
| Activating oncogenes? | Yes | Yes | Yes |
| Elevated FOXN1? | Yes | Yes | No |
| P53 wild-type? | Yes | Yes | No |
| Akt pathway active? | Yes | Yes | ? |
| FGFR3/PI3K mutations? | Yes | Yes | ? |
| Involution by apoptosis? | Yes | Yes | |
| Response to A44/puro? | ? | Yes | ? |
| | KA v. SK: 7/10 | SK v. SCC: 1/10 | KA v. SCC: 3/10 |

What is claimed is:

1. A method of treating a keratoacanthoma in a subject, the method comprising
   (a) receiving the results of an assay distinguishing a keratoacanthoma cell(s) from a squamous cell carcinoma in a skin sample, wherein the results are generated by the steps of:
      (i) assaying a level of FOXN1 in a skin sample obtained from a subject, wherein the skin sample is a skin biopsy taken from the part of the skin suspected of having a keratoacanthoma;
      (ii) detecting an increase in the level of FOXN1 of at least 10% as compared to the level of FOXN1 in a sample of normal skin cells, thereby detecting a keratoacanthoma cell(s) in the skin sample, and
   (b) administering a therapeutically effective amount of a composition comprising kaempferol, ellipticine, nutlin-3 or pyromycin to the subject.

2. The method of claim 1, wherein the level of FOXN1 is measured by an immunoassay.

3. The method of claim 1, wherein the level of FOXN1 is measured by measuring a level of FOXN1 mRNA.

4. The method of claim 3, wherein the level of FOXN1 mRNA is measured by reverse transcription-polymerase chain reaction (RT-PCR).

* * * * *